United States Patent
Shankar et al.

(10) Patent No.: US 8,717,026 B2
(45) Date of Patent: May 6, 2014

(54) MAGNETIC FIELD DETECTION DEVICE

(75) Inventors: Ira Shankar, Katy, TX (US); Ashok Nedungadi, Lake Oswego, OR (US)

(73) Assignee: BIOTRONIK CRM Patent AG (CH)

( * ) Notice: Subject to any disclaimer, the term of this patent is extended or adjusted under 35 U.S.C. 154(b) by 733 days.

(21) Appl. No.: 12/762,450

(22) Filed: Apr. 19, 2010

(65) Prior Publication Data

US 2010/0308830 A1 Dec. 9, 2010

Related U.S. Application Data

(60) Provisional application No. 61/184,345, filed on Jun. 5, 2009.

(51) Int. Cl.
*G01V 3/00* (2006.01)

(52) U.S. Cl.
USPC .......................................... 324/318

(58) Field of Classification Search
USPC ................................. 324/300–322
See application file for complete search history.

(56) References Cited

U.S. PATENT DOCUMENTS

| | | | |
|---|---|---|---|
| 5,179,429 A | 1/1993 | Ristic et al. | |
| 5,438,990 A | 8/1995 | Wahlstrand et al. | |
| 6,150,809 A * | 11/2000 | Tiernan et al. | 324/238 |
| 6,510,345 B1 | 1/2003 | Van Bentem et al. | |
| 6,963,779 B1 | 11/2005 | Shankar et al. | |
| 7,936,168 B2 * | 5/2011 | Crozier et al. | 324/247 |
| 8,217,647 B2 * | 7/2012 | Dittmer et al. | 324/260 |
| 8,217,654 B2 * | 7/2012 | Biber et al. | 324/318 |
| 8,416,076 B2 * | 4/2013 | Mamourian et al. | 340/551 |
| 8,423,133 B2 * | 4/2013 | Doerr et al. | 607/2 |
| 8,423,135 B2 * | 4/2013 | Doerr et al. | 607/4 |
| 2008/0154342 A1 | 6/2008 | Digby et al. | |

FOREIGN PATENT DOCUMENTS

EP  1 935 450  5/2008

\* cited by examiner

*Primary Examiner* — Dixomara Vargas
(74) *Attorney, Agent, or Firm* — Craig A. Fieschko, Esq.; DeWitt Ross & Stevens S.C.

(57) ABSTRACT

A magnetic field sensor device suitable for use in an implantable medical device (such as a pacemaker, cardioverter/defibrillator, or cardiac resynchronization therapy device) is able to detect magnetic fields, such as the fields generated by a Magnetic Resonance Imaging (MRI) device, over a wide measurement range and to discriminate between different field strengths. Multiple sensors provided within the magnetic field sensor device are optimally biased to provide a power saving solution which is accurate enough for medical devices applications. The output of the magnetic field sensor device can be used to switch the implantable medical device to different operational modes, e.g., between programmable and "MRI safe" modes.

20 Claims, 8 Drawing Sheets

MAGNETIC FIELD DETECTION DEVICE

CROSS-REFERENCE TO RELATED APPLICATIONS

This application claims priority under 35 USC §119(e) to U.S. Provisional Patent Application 61/184,345 filed Jun. 5, 2009, the entirety of which is incorporated by reference herein.

FIELD OF THE INVENTION

The invention relates to an improved magnetic field detection device, and in particular to an improved magnetic field detection device for recognizing magnetic field strength over several magnitudes.

BACKGROUND OF THE INVENTION

Magnetic resonance imaging, further referred to as MRI, is of increasing relevance for modern diagnosis. Up to now active implanted medical devices (active IMDS), such as (but not restricted to) pacemakers, cardioverters/defibrillators, and cardiac resynchronization therapy devices, prevent effective utilization of MRI technology for diagnosis. Even the newly-presented so-called "MRI conditional" implants pose difficulties insofar as such devices have to be switched to a so-called "MRI safe" mode, which requires at least a consultation with a heart specialist before and after the MRI examination (if not requiring the presence of a heart specialist during the entire MRI examination).

These problems can be overcome by a reliable detection of MRI fields and appropriate programming of the active IMDs, as described in EP 1 935 450 by Digby et al. or by Shankar et al. in U.S. Pat. No. 6,963,779. Wahlstrand et al. disclose in U.S. Pat. No. 5,438,990 the use of a so called MagFET, a magnetic field effect transistor or magnetic field sensitive MOSFET as a reed switch. U.S. Pat. No. 5,179,429 to Ristic et al. discloses a magnetic field sensor based on a bipolar transistor with split collector contacts. Also known in the art is the use of hall sensors replacing the reed switch and enabling the device to detect the strength of a magnetic field, as in U.S. Pat. No. 6,510,345 Van Bentem et al.

These solutions still have power consumption which is unsuitable for use in a medical device. Therefore, it is an object of the invention to provide a sensor device accurate enough to discriminate between different magnitudes of a magnetic field, while at the same time consuming less power than prior solutions.

SUMMARY OF THE INVENTION

The invention provides a sensor device able to detect magnetic fields over a wide measurement range, and to discriminate between different field strengths of the magnetic fields. For high field detection, the device includes at least a Mag-FET sensor or a magnetotransistor or a hall sensor, and for low field detection the device includes a reed is switch or a hall sensor or a GMR (giant magnetoresistance) sensor. Furthermore, the device generates different signals depending on the magnetic field strengths. For purposes of this document, the measurement of field strength below a predefined threshold, or below the sensitivity of the sensor for low magnetic fields, will be referred to as the detection or sensing of effectively no magnetic field. The phrase "detection of a magnetic field" should be understood as detecting a field, and in the case of using a MagFET sensor, a hall sensor, a magnetotransistor or a GMR sensor, should be understood as detecting and/or measuring the magnitude or field intensity of a magnetic field.

"MagFET sensor" does not refer only to a sensor with one sensor element, but also refers to a sensor with two or more sensor elements. In particular, an array of three sensor elements is preferred because it can sense magnetic fields in all three spatial directions.

The combination of a reed switch or a hall sensor or a GMR sensor for low field detection, and a MagFET sensor or hall sensor or a magnetotransistor for high field detection, allows a reduction of power consumption and an enhancement of measurement accuracy, because the different sensors can work, or more precisely measure, in a measurement range they are optimized for. The reed switch is a preferred element for low field detection for field strengths exceeding 1 mT, preferably in the range of 1 mT to 3 mT, while MagFET sensors or hall sensors or magnetotransistors are more suitable for high field detection in the order of a few tesla.

Also preferred is that the magnetic field detection is carried out by a reed switch for low magnetic fields, by a MagFET sensor for out-of-plane components of high magnetic DC fields, and by a magnetotransistor for in-plane components of high magnetic DC fields.

In another version of the invention, either the combination of a reed switch for low magnetic field detection and a Mag-FET for high magnetic field detection, or the combination of a reed switch for low magnetic field detection and a MagFET and a magnetotransistor for high magnetic field detection, is additionally combined with a high frequency coil or a communication antenna and/or a RF antenna to detect the presence of high frequency magnetic fields. High frequency magnetic fields in addition to high DC magnetic fields are a good and common indicator of the presence of a MRI apparatus.

In a preferred version of the invention, the sensor for low field detection is a reed switch susceptible to field strengths exceeding 1 mT.

In a further preferred version of the invention, the low field detection is sensitive to magnetic field strength between 1.0 mT and 2.5 mT, preferably between 1.5 mT and 2.0 mT, and the MagFET sensor and/or magnetotransistor for high field detection is sensitive to magnetic field strengths between 0.5 T and 7.0 T.

It is also preferred that the different signals generated by the device include generating a first signal if detecting a low magnetic field between 0.5 mT and 2.0 mT, generating a second signal if detecting a high magnetic field exceeding 1.0 T, and generating a third signal for a magnetic field below 1.0 mT. The signal(s) may be transmitted to a unit controlling the mode of a device incorporating the magnetic field detection device.

The invention also involves an implantable medical device with a magnetic field detection device including at least a MagFET sensor and/or a magnetotransistor for detecting high magnetic fields exceeding 0.5 T, and a reed switch or a hall sensor for detecting low magnetic fields exceeding 2.0 mT, preferably exceeding 1 mT.

It is preferred to use a magnetotransistor to detect in-plane components of the static (DC) magnetic field, and a MagFET to detect the out-of-plane component of the static magnetic field. It is further preferred that both sensors are integrated in/on the same circuit board or integrated circuit so that they measure magnetic field components which are orthogonal to each other.

In another variation of the invention, two or more MagFET sensors or magnetotransistor sensors are arranged on an ultra high density circuit board which is nonplanar in such a way that the two or more sensors measure different vectors or components of the magnetic field, preferably orthogonal components of the magnetic field.

In a preferred version the magnetic field detection device includes means for generating a first signal if detecting a low magnetic field, and means for generating a second signal if detecting a high magnetic field. These signals may be, but are not restricted to, control signals to alter the operation mode of the implantable medical device.

Also preferred is that the detection of a low magnetic field triggers switching of the implantable medical device to a first mode, and detection of a high magnetic field triggers switching to a second mode. The first mode may be a mode enabling programming of the implantable medical device, and the second mode may be a MRI safe mode.

Also preferred is that the MRI safe mode includes switching to a 000, V00 or D00 mode and/or inhibiting the delivery of a high energy shock. In these modes, the first character stands for the pacing mode and the second character stands for the sensing mode (0 means no pacing/sensing, V means ventricular pacing/sensing, and D means dual pacing/sensing in the atrium and the ventricle), and the third character represents the reaction to the sensing (0 means no reaction).

Furthermore, the invention includes a method for detecting magnetic fields over several orders of magnitude, characterized in that the low detectable magnetic field strength is measured by a reed switch or a hall sensor or a GMR sensor, and the high detectable magnetic field strength is measured by a MagFET sensor and/or a magnetotransistor, and different signals are generated depending on the measured magnetic field strength. The method preferably additionally includes combining the high magnetic field detection with a high frequency coil, a communication antenna, and/or a RF antenna to detect the presence of high frequency magnetic fields which are present during a MRI examination.

Preferably, detection of a low magnetic field triggers switching of an implanted medical device to a first mode, and detection of a high magnetic field triggers switching of the device to a second mode.

Also preferred is that the first mode is a mode enabling programming of the implantable medical device, and the second mode is a MRI safe mode.

BRIEF DESCRIPTION OF THE DRAWINGS

Some possible exemplary aspects of the invention are illustrated in FIGS. 1 to 7, which show.

DETAILED DESCRIPTION OF THE INVENTION

Figure 1:
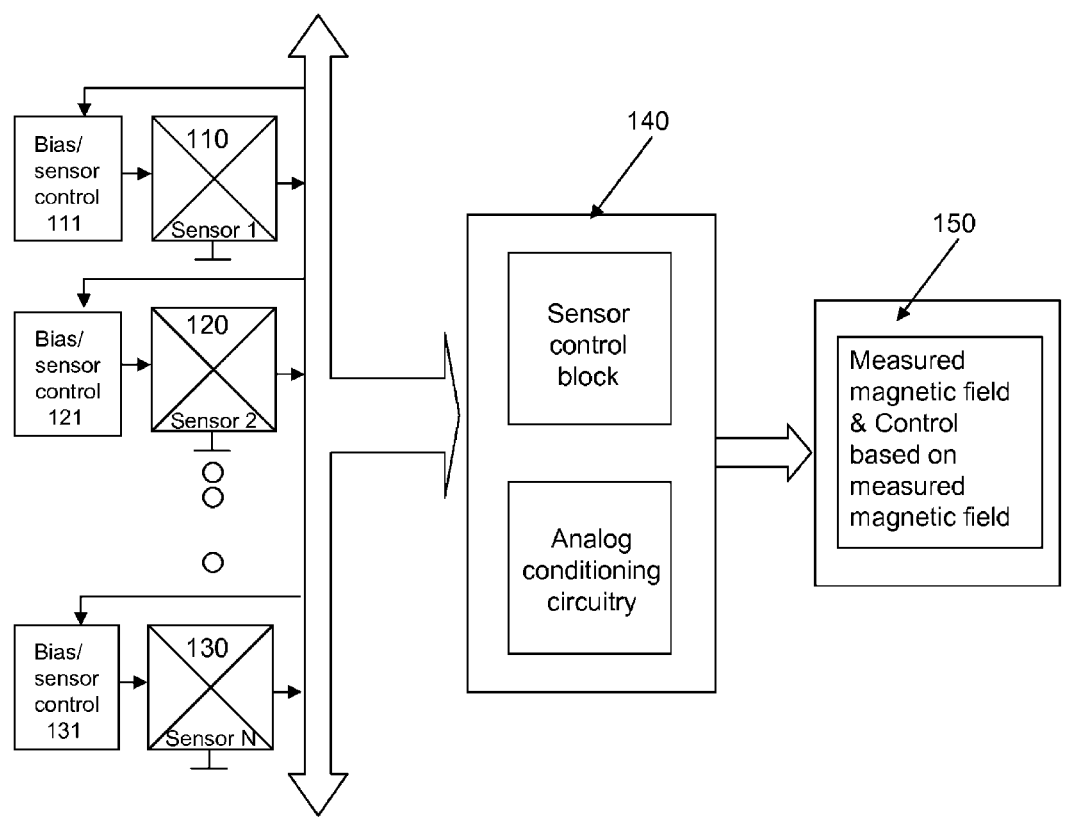
FIG. 1 a schematic view of a multi-sensor system for detecting magnetic fields.

FIG. 1 shows a schematic view of a multi-sensor system in accordance with the invention. The different sensors 110, 120 and 130 are controlled via a bias/sensor control 111, 121 and 131, and are optimally biased for their working point. Therefore, energy consumption is minimized. The sensors are connected with the control block 140, comprising a sensor control block and an analog conditioning circuit, which delivers the field measurement and/or a control signal based on the measured magnetic field.

Figure 2:
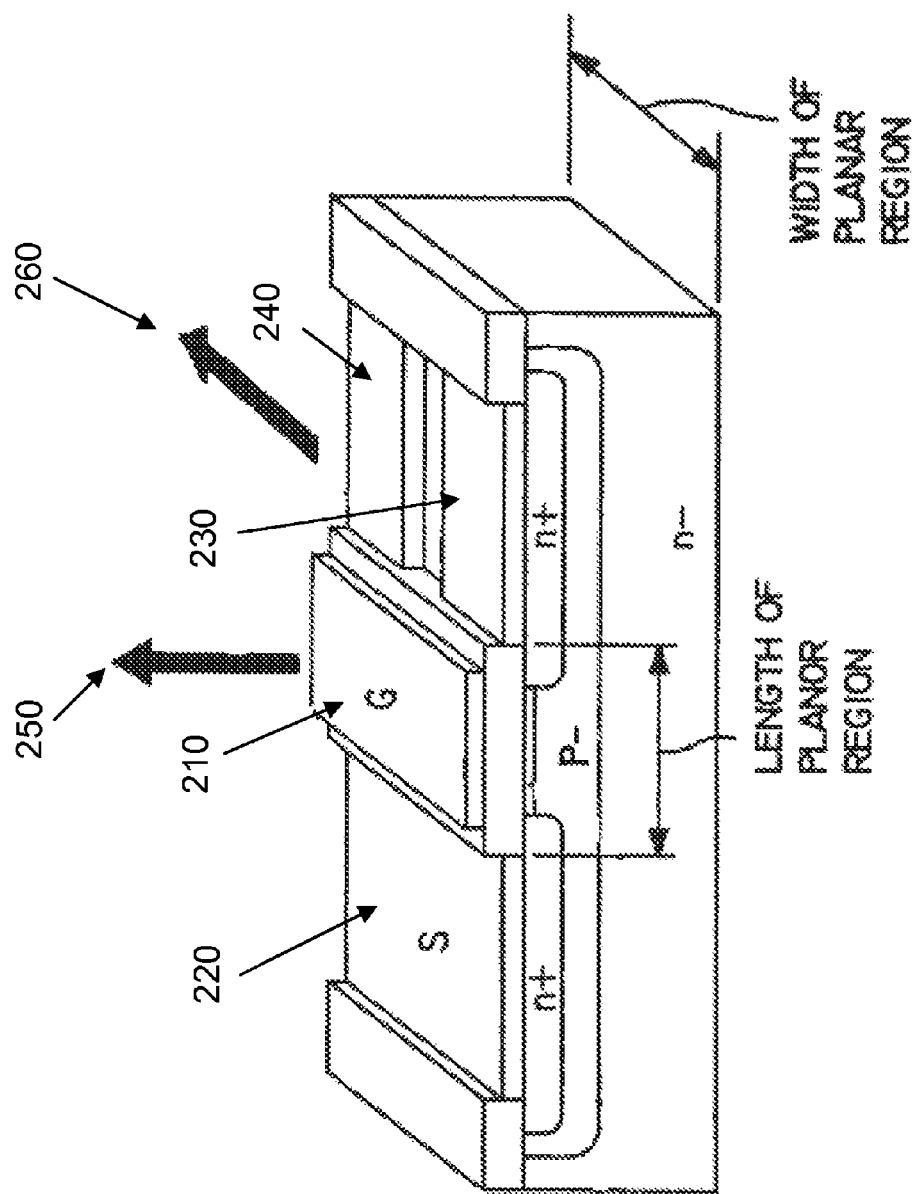
FIG. 2 a perspective view of a N-channel MagFET.

The assembly of a dual drain n-channel MagFET is schematically shown in a perspective view in FIG. 2. When operated in a magnetic field perpendicular to the channel or gate 210 of the electrical signal, such a field being identified with the arrow 250, the currents measured between the source 220 and drain 230 or 240 differ from each other because of the force (identified by arrow 260) affecting the charge carriers. The difference in the current is a measurement of the magnetic field. The basic functions of a MagFET are well known by a person ordinary skilled in the art.

Figure 3:
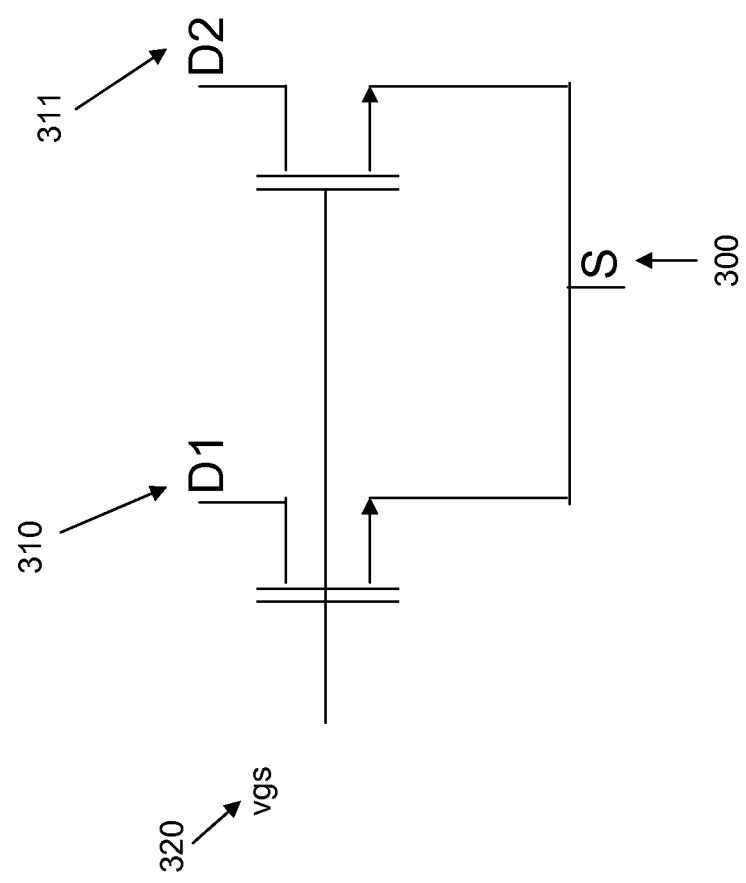
FIG. 3 a schematic representation of a split drain MagFET.

FIG. 3 shows a schematic representation of a split drain n-channel MagFET, with the two different drains D1 (310) and D2 (311), a common source 300, and gate 320.

Figure 4A:
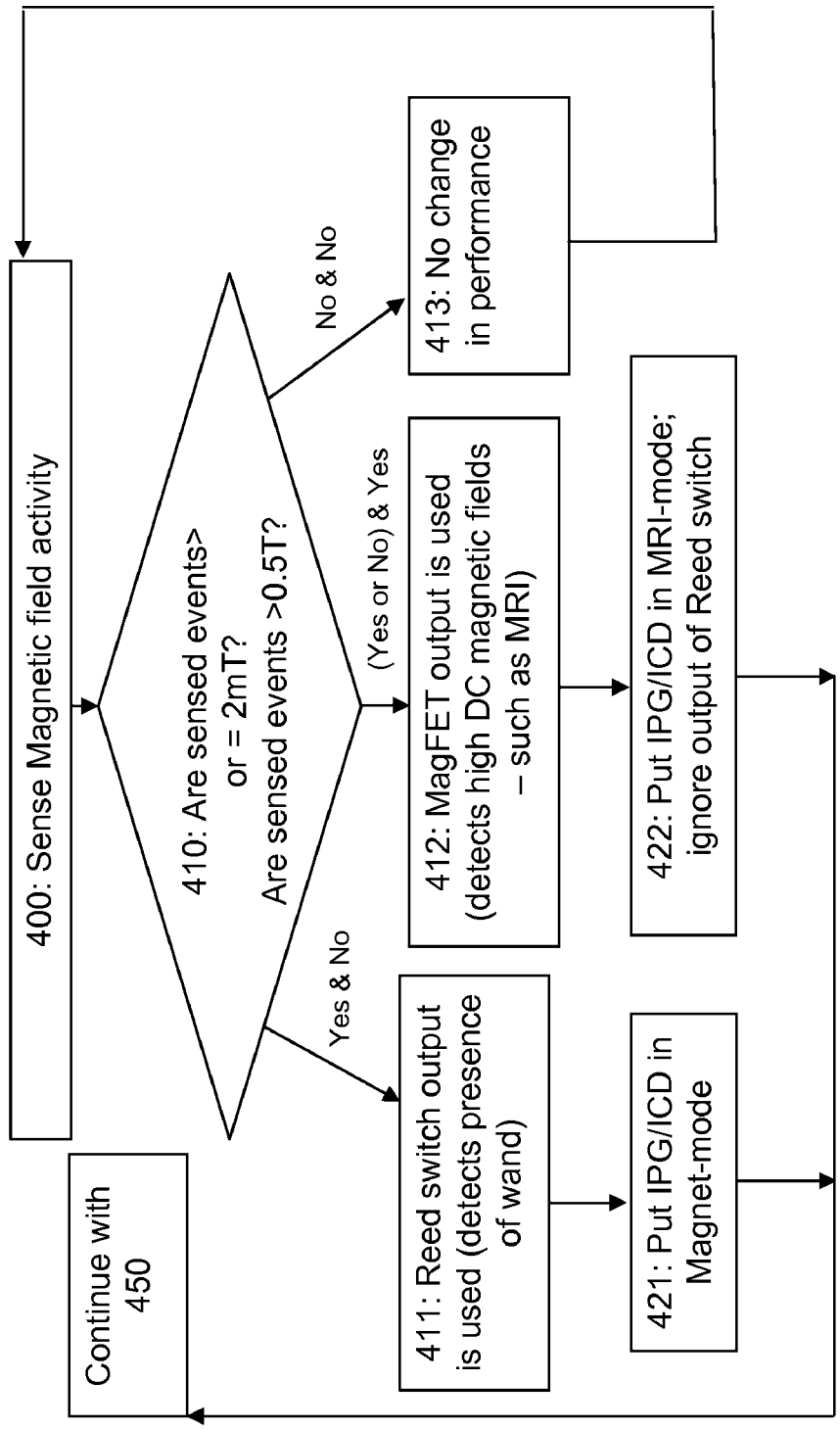
FIG. 4a an exemplary flowchart of a magnetic detection device.
Figure 4B:
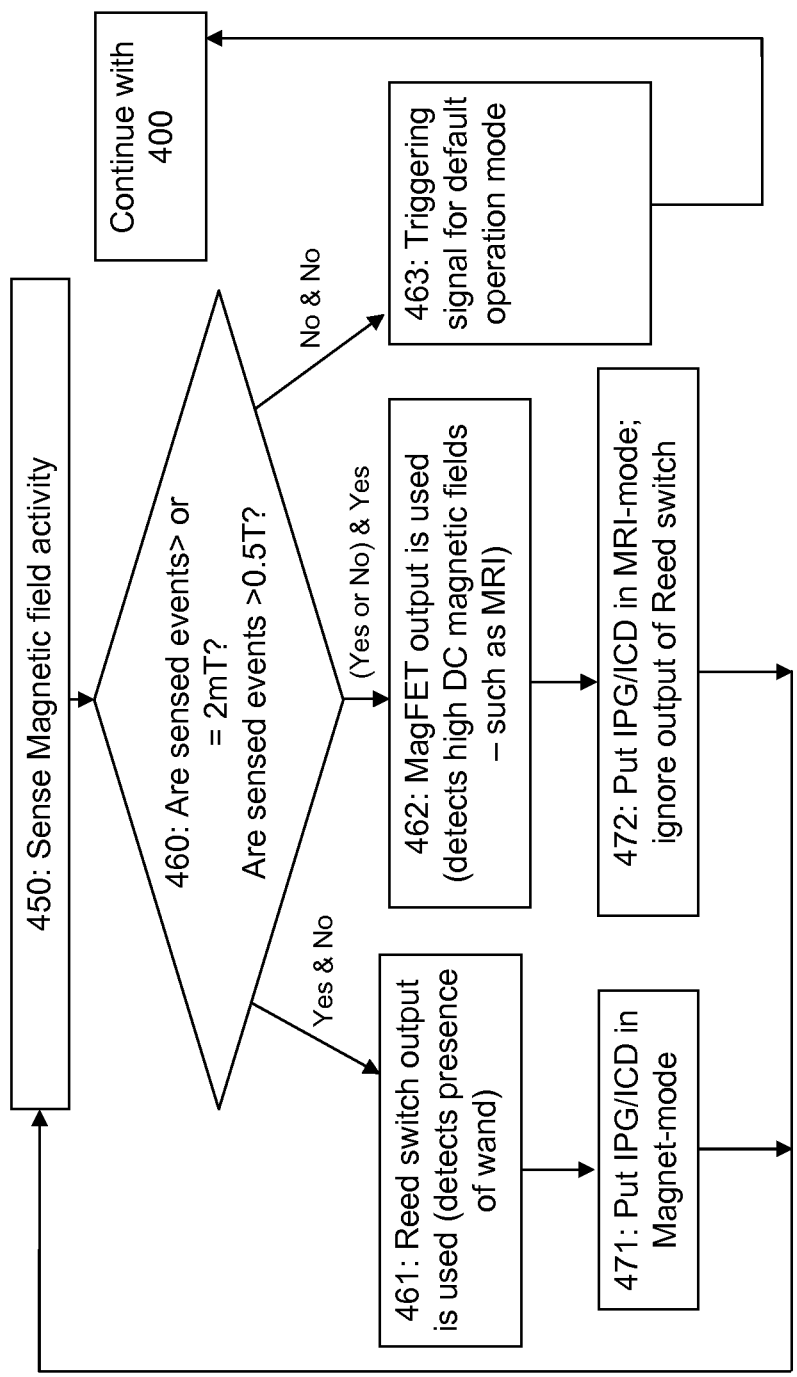
FIG. 4b an exemplary flowchart of a magnetic detection device.

The flow charts of FIGS. 4a-4b show basic functions of an exemplary magnetic field detection device. FIG. 4a illustrates operation where no reasonable magnetic field was detected during the previous measurement (where "reasonable" means there was no field detected exceeding a certain threshold, such as but not limited to 1.7 mT or 1.9 mT). After measuring of magnetic field activity at 400, it is decided whether the detected field is equal to or exceeding 2 mT, and/or whether the detected field is exceeding 0.5 T, or whether no reasonable magnetic fields has been sensed. In the case at 411 in which the measured magnetic field is equal to or exceeding 2 mT (but not exceeding 0.5 T), the reed switch or low field sensor output is used to trigger a signal 421 for initiating a first operation mode such as (but not limited to) a so called magnet-mode or programming mode. A subsequent measurement 450 is then performed as per the flow chart 4b.

In the case at 412 in which the measured magnetic field is equal to or exceeds 2 mT and exceeds 0.5 T, the MagFET sensor or high field sensor output is used to trigger a signal 422 for initiating a second mode such as (but not limited to) a so called MRI-safe mode. The subsequent measurement 450 is then performed as per the flow chart 4b.

As per step 413, if neither a magnetic field equal to nor exceeding 2 mT, nor exceeding 0.5 T, has been sensed, sensing will be continued with step 400.

FIG. 4b illustrates the operation of the device, if in the previous measurement a magnetic is field has been sensed which is equal to or exceeding a certain threshold (such as 2.0 mT) and/or is exceeding a second threshold (such as 0.5 T). In these cases, after measurement 450, it is decided whether a field is equal to or exceeding 2 mT, and/or whether a field is exceeding 0.5 T, or whether no reasonable magnetic field has been sensed. In the case 461 in which the measured magnetic field is equal to or exceeding 2 mT, but not exceeding 0.5 T, the reed switch or low field sensor output is used to trigger a signal 471 for initiating a first operation mode such as (but not limited to) a so-called magnet-mode or programming mode. The subsequent measurement 450 is performed following the flow chart 4b.

In the case 462 in which the measured magnetic field is equal to or exceeding 2 mT and also exceeding 0.5 T, the MagFET sensor or high field sensor output is used to trigger a signal 472 for initiating a second mode such as (but not limited to) a so-called MRI-safe mode. The subsequent measurement 450 is performed following the flow chart 4b.

If neither a magnetic field equal nor exceeding 2 mT nor exceeding 0.5 T has been sensed, and a signal 463 for initiating switching to the default mode is triggered, sensing will be continued with step 400.

Figure 5:
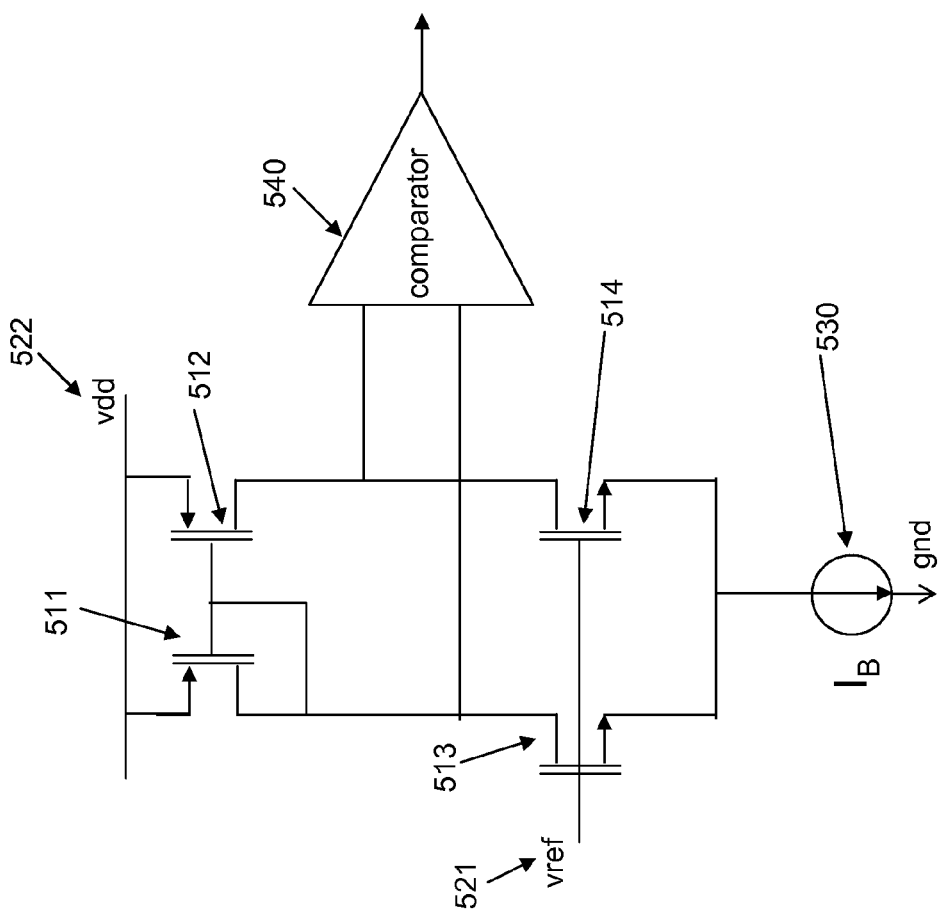
FIG. 5 a schematic illustration of a MagFET in a magnetic sensor.

FIG. 5 shows a schematic illustration of a magnetic sensor utilizing a p-channel 513, 514 and/or a n-channel 511, 512 MagFET. The differences in the drain currents are evaluated by a comparator 540. In FIGS. 4a-4b, under high field conditions (exceeding 0.5T), the reed switch may not necessarily be closed. Therefore, owing to lack of detection of the reed switch, it cannot be concluded that no magnetic field is present.

Figure 6:
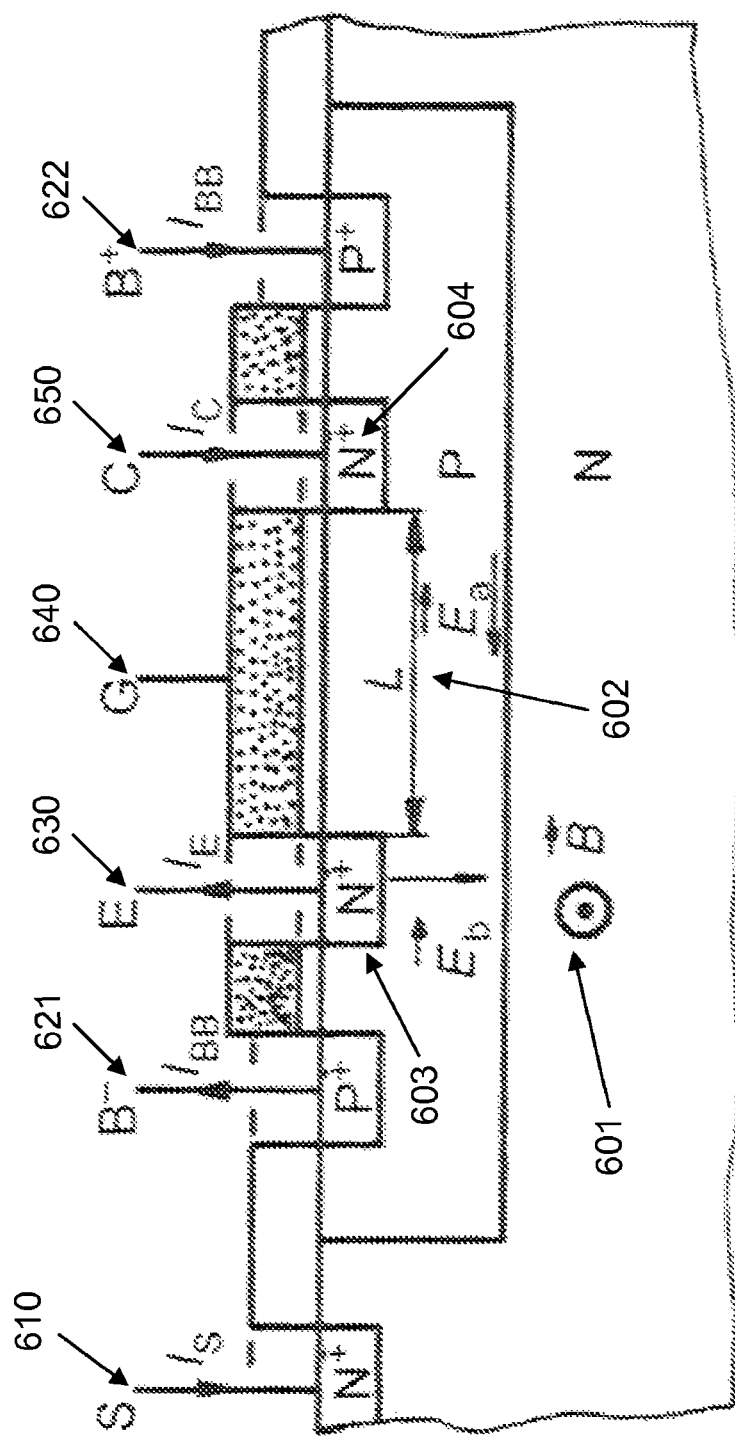
FIG. 6 a cross section of a Lateral Magneto-transistor in CMOS technology.

FIG. 6 shows a cross-section of a lateral magnetotransistor in CMOS technology, as is appropriate to combine with a MagFET to improve sensitivity. The assumed magnetic field, B vector, is represented at 601. The magnetotransistor is a bipolar transistor implemented on a semiconductor surface whose structure and operating conditions are appropriately selected and optimized to boost magnetic sensitivity of its collector current.

FIG. 6 shows a typical lateral magnetotransistor manufactured in a p-well (base 602) wherein a voltage is applied to the two base contacts, B+(622) and B−(621), to accelerate the minority carrier injection into the base 602 region. The two n+ regions 603 and 604, separated by the length L of the lateral base 602, serve as the Emitter E (630) and Collector C (650) of the magnetotransistor. Assuming that the magnetotransistor is adequately forward-biased, in the absence of magnetic field the electrons are injected into the base region 602 by the emitter 630 and drift mainly along the base length and are collected by collector C (650), producing collector current $I_c$. Some electrons diffuse downwards and are collected by the secondary collector S (610), producing the substrate current $I_s$. In the absence of a magnetic field and adequate bias conditions, the ratio of $I_c/I_s$ is constant. Applying a magnetic field B perpendicular to the magnetotransistor, not shown, causes the electrons to be deflected towards the substrate region and therefore very few electrons contribute to the collector current $I_c$. This causes a very small change in the ratio of $I_c/I_s$. In the presence of a magnetic field B (601) in the plane of the magnetotransistor in FIG. 6, the electrons are deflected towards the device surface, causing the collector current $I_c$, to increase. This causes an appreciable change in the ratio of $I_c/I_s$, which can be measured to get a measure of the applied magnetic field.

Figure 7:
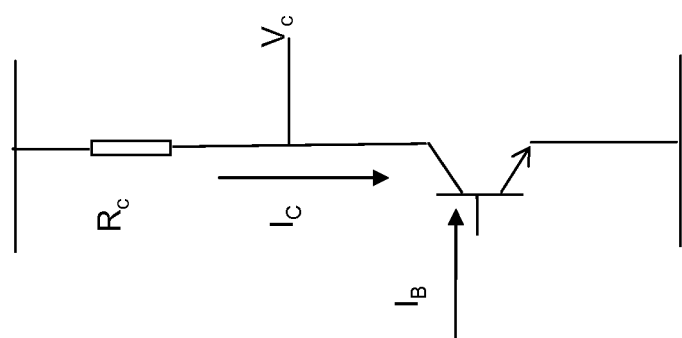
FIG. 7 a schematic representing a MagBJT circuit.

A schematic representation of a magnetotransistor is shown in FIG. 7, indicating the collector and base currents with arrows.

The scope of the invention is not limited to above-mentioned exemplary versions of the invention. A person skilled in the art will understand that the various versions of the methods and devices are related to each other, so that combinations of the versions are also encompassed within the scope of the invention.

It will be apparent to those skilled in the art that numerous modifications and variations of the described examples and versions are possible in light of the foregoing discussion. The disclosed examples and versions are presented for purposes of illustration only. Therefore, it is the intent to cover all such modifications and alternate versions as may come within the true scope of this invention.

What is claimed is:

1. A magnetic field detection device for detecting magnetic fields and discriminating field strengths, the device including:
   a. a high field detection sensor including one or more of:
      (1) a MagFET sensor,
      (2) a magnetotransistor, and
      (3) a hall sensor;
   b. a low field detection sensor including one or more of:
      (1) a reed switch,
      (2) a hall sensor, and
      (3) a GMR sensor,
   wherein the device generates output signals which differ in dependence on the magnetic field strengths.

2. The device of claim 1 wherein the low field detection sensor is a reed switch changing between open and closed states at field strengths exceeding 1 mT.

3. The device of claim 1 wherein:
   a. the low field detection sensor is sensitive to magnetic field strengths between 1.0 mT and 2.5 mT, and
   b. the high field detection sensor is sensitive to magnetic field strengths between 0.5 T and 7.0 T.

4. The device of claim 3 wherein the low field detection sensor is sensitive to magnetic field strengths between 1.5 mT and 2.0 mT.

5. The device of claim 1 wherein:
   a. the device emits a first signal if detecting magnetic field strengths between 1.0 mT and 2.0 mT, and
   b. the device emits a second signal if detecting magnetic field strengths above 0.5 T.

6. The device of claim 1 wherein:
   a. the low field detection sensor includes a reed switch, and
   b. the high field detection sensor includes a MagFET sensor.

7. The device of claim 6 further including one or more of:
   a. a high frequency coil,
   b. a communication antenna, and
   c. a RF antenna,
   in communication with one or more of the detection sensors for detecting the presence of high frequency magnetic fields.

8. The device of claim 6 wherein:
   a. the high field detection sensor further includes a magnetotransistor, and
   b. the MagFET sensor and magnetotransistor are aligned with respect to each other such that:
      (1) the MagFET sensor detects out-of-plane components of high magnetic DC fields, and
      (2) the magnetotransistor detects in-plane components of high magnetic DC fields.

9. The device of claim 8 further including one or more of:
   a. a high frequency coil,
   b. a communication antenna, and
   c. a RF antenna,
   in communication with one or more of the detection sensors for detecting the presence of high frequency magnetic fields.

10. A magnetic field detection device for detecting magnetic fields and discriminating field strengths, the device including:
    a. a high field detection sensor including one or more of:
       (1) a MagFET sensor,
       (2) a magnetotransistor, and
       (3) a hall sensor;
    b. a low field detection sensor including one or more of:
       (1) a reed switch,
       (2) a hall sensor, and
       (3) a GMR sensor,
    wherein:
    i. the device generates output signals which differ in dependence on the magnetic field strengths,
    ii. the magnetic field detection device is provided on or within an implantable medical device, iii. the implantable medical device delivers electrical stimulation to a heart at least partially in response to the output signals of the magnetic field detection device.

11. An implantable medical device having a magnetic field detection device for detecting magnetic fields and discriminating field strengths, the magnetic field detection device including:
 a. a low field detection sensor including one or more of:
  (1) a reed switch, and
  (2) a hall sensor,
  detecting magnetic field strengths exceeding 1 mT, and
 b. the high field detection sensor including one or more of:
  (1) a MagFET sensor, and
  (2) a magnetotransistor,
  detecting magnetic field strengths exceeding 0.5 T,
 wherein:
  i. the implantable medical device receives output signals of the implantable medical device,
  ii. the output signals differ in dependence on the magnetic field strengths.

12. The device of claim 11 wherein:
 a. a first signal is generated if a low magnetic field having strength exceeding 1 mT is detected, and
 a. a second signal is generated if a high magnetic field having strength exceeding 0.5 T is detected.

13. The device of claim 11 wherein:
 a. detection of a low magnetic field having strength exceeding 1 mT switches the implantable medical device to a first mode, and
 a. detection of a high magnetic field having strength exceeding 0.5 T switches the implantable medical device to a second mode.

14. The device of claim 13 wherein:
 a. the first mode is a mode enabling programming of the implantable medical device, and
 b. the second mode is a MRI safe mode.

15. The device of claim 14 wherein the MRI safe mode switches to one of a 000, V00 or D00 mode.

16. The device of claim 14 wherein the MRI safe mode inhibits the delivery of a high energy shock from the implantable medical device.

17. A method for detecting magnetic fields and discriminating field strengths over several orders of magnitude, the method including the steps of:
 a. detecting any high-strength magnetic fields present with use of one or more of:
  (1) a MagFET sensor,
  (2) a magnetotransistor, and
  (3) a hall sensor;
 b. detecting any low-strength magnetic fields present with use of one or more of:
  (1) a reed switch,
  (2) a hall sensor, and
  (3) a GMR sensor,
 c. emitting an output signal in dependence on the detected magnetic field strength.

18. The method of claim 17 further including the step of:
 a. switching an implanted medical device to a first mode upon detection of a low-strength magnetic field, and
 b. switching the implanted medical device to a second mode upon detection of a high-strength magnetic field.

19. A method for detecting magnetic fields and discriminating field strengths over several orders of magnitude, the method including the steps of:
 a. detecting any high-strength magnetic fields present with use of one or more of:
  (1) a MagFET sensor,
  (2) a magnetotransistor, and
  (3) a hall sensor;
 b. detecting any low-strength magnetic fields present with use of one or more of:
  (1) a reed switch,
  (2) a hall sensor, and
  (3) a GMR sensor,
 c. switching an implanted medical device to a first mode upon detection of a low-strength magnetic field, wherein the first mode is a mode enabling programming of the implantable medical device, and
 d. switching the implanted medical device to a second mode upon detection of a high-strength magnetic field, wherein the second mode is a MRI safe mode.

20. A method for detecting magnetic fields and discriminating field strengths over several orders of magnitude, the method including the steps of:
 a. detecting any high-strength magnetic fields present with use of one or more of:
  (1) a MagFET sensor,
  (2) a magnetotransistor, and
  (3) a hall sensor;
 b. detecting any low-strength magnetic fields present with use of one or more of:
  (1) a reed switch,
  (2) a hall sensor, and
  (3) a GMR sensor;
 c. emitting an output signal in dependence on the detected magnetic field strength;
 d. delivering electrical stimulation to a heart at least partially in response to the output signal of the magnetic field detection device.

* * * * *